United States Patent
Kocourek et al.

(10) Patent No.: US 9,174,181 B2
(45) Date of Patent: Nov. 3, 2015

(54) DISPOSABLE BIOREACTOR FOR CULTURING CELLS IN A NUTRIENT MEDIUM

(75) Inventors: Andreas Kocourek, Bielefeld (DE); Christopher Biddell, Stonehouse (GB); Oscar-Werner Reif, Hannover (DE); Florian Wurm, Le-Mont-sur-Lausanne (CH)

(73) Assignee: Sartorius Stedim Biotech GmbH (DE)

(*) Notice: Subject to any disclaimer, the term of this patent is extended or adjusted under 35 U.S.C. 154(b) by 949 days.

(21) Appl. No.: 12/086,318

(22) PCT Filed: Dec. 20, 2006

(86) PCT No.: PCT/EP2006/012274
§ 371 (c)(1),
(2), (4) Date: Jun. 10, 2008

(87) PCT Pub. No.: WO2007/079936
PCT Pub. Date: Jul. 19, 2007

(65) Prior Publication Data
US 2009/0311775 A1    Dec. 17, 2009

(30) Foreign Application Priority Data
Dec. 22, 2005 (DE) .......... 10 2005 062 052

(51) Int. Cl.
*C12M 3/00* (2006.01)
*B01F 13/00* (2006.01)
*B01F 11/00* (2006.01)
*B01F 15/00* (2006.01)
*B01L 3/00* (2006.01)
(Continued)

(52) U.S. Cl.
CPC .......... *B01F 13/0022* (2013.01); *B01F 11/0094* (2013.01); *B01F 15/00902* (2013.01); *B01L 3/5082* (2013.01); *C12M 23/08* (2013.01); *C12M 23/28* (2013.01); *C12M 27/20* (2013.01); *B01F 13/002* (2013.01); *B01L 2300/0858* (2013.01)

(58) Field of Classification Search
CPC ........ B01F 11/94; B01F 13/22; B01F 15/902; C12M 27/20; C12M 23/08; C12M 23/28; B01L 3/5082; B01L 2300/858; Y10S 215/08; Y10T 29/49382; D06B 3/28
USPC ................ 435/304.2, 299.2, 288.2
See application file for complete search history.

(56) References Cited

U.S. PATENT DOCUMENTS 3,578,291 A    5/1971   Oberli
4,083,207 A *  4/1978   Ekstroem .................. 68/178
(Continued)

FOREIGN PATENT DOCUMENTS

DE    597567      5/1934
DE    1 140 755   12/1962
(Continued)

*Primary Examiner* — William H Beisner
*Assistant Examiner* — Danielle Henkel
(74) *Attorney, Agent, or Firm* — Gerald E. Hespos; Michael J. Porco; Matthew T. Hespos

(57) ABSTRACT

Disposable bioreactor for culturing cells in a nutrient medium, consisting of a reagent container which is sealable with a lid and which is capable of being subjected to a shaking process in a shaking device, where the reagent container is equipped with at least one web adjacent to the internal wall of the container, the web being arranged running vertically from the bottom upward, preferably in the shape of a helix.

8 Claims, 2 Drawing Sheets

Figure 3:
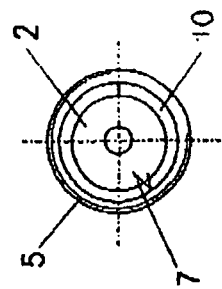

(51) Int. Cl.
*C12M 1/24* (2006.01)
*C12M 1/00* (2006.01)

(56) References Cited

U.S. PATENT DOCUMENTS

| | | | |
|---|---|---|---|
| 4,912,048 A | | 3/1990 | Smith et al. |
| 5,075,234 A | * | 12/1991 | Tunac ................... 435/301.1 |
| 5,116,758 A | | 5/1992 | Verma |
| 5,358,872 A | * | 10/1994 | Mussi et al. ............. 435/297.1 |
| 5,374,557 A | | 12/1994 | Verma |
| 5,958,778 A | | 9/1999 | Kidd |
| 6,503,455 B1 | | 1/2003 | Kidd |

FOREIGN PATENT DOCUMENTS

| | | | | |
|---|---|---|---|---|
| DE | 21 34 808 | | 5/1975 | |
| DE | 28 50 548 | | 6/1980 | |
| EP | 0 819 941 B1 | | 8/2003 | |
| FR | 2 740 758 | | 5/1997 | |
| JP | 06-253815 A | | 9/1994 | |
| WO | WO 96/30274 | | 10/1996 | |
| WO | WO98/51412 | * | 11/1998 | ............ B01L 3/14 |
| WO | WO 98/51412 | | 11/1998 | |

* cited by examiner

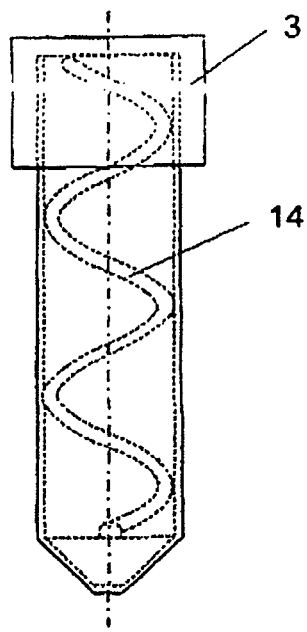
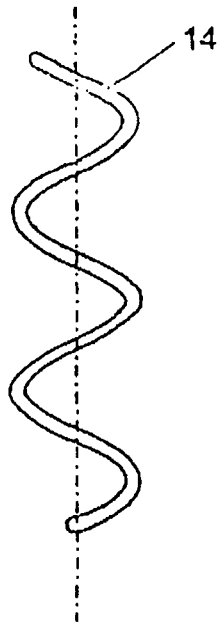
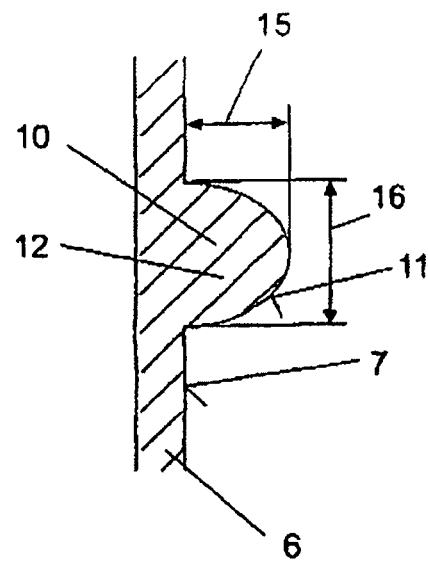
Fig. 4      Fig. 5      Fig. 6
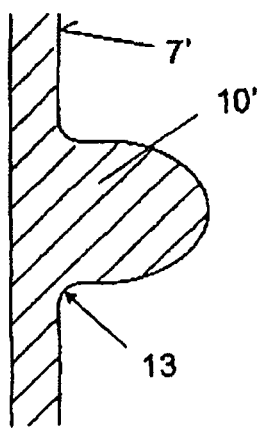
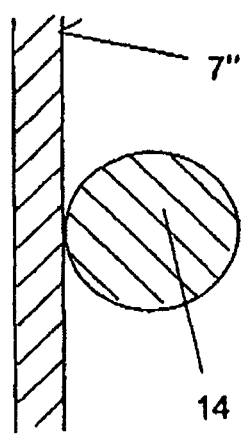
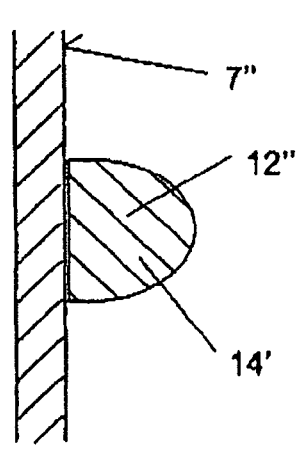
Fig. 7      Fig. 8      Fig. 9

DISPOSABLE BIOREACTOR FOR CULTURING CELLS IN A NUTRIENT MEDIUM

This invention relates to a disposable bioreactor for cultivation of cells in a nutrient medium, consisting of a reagent container which is sealable with a lid and which is subjectable to a shaking operation in a shaking apparatus, the reagent container having at least one chicane or baffle adjacent the container's inner wall.

Disposable bioreactors are known for cultivation of cells in a nutrient medium having a cell culture volume of about 5 ml to 50 l. When such systems are used on a small scale with offline monitoring, the processing conditions need to be optimized. A bioprocess is characterized by pH changes, oxygen input, release of $CO_2$ and other biological and physicochemical parameters. For mixing, which is frequently necessary, the disposable bioreactors are for example subjected to a shaking operation in a shaking apparatus. The mixing time in the case of such bioreactor systems on a small scale is an important factor in relation to mass transfer. Especially the gas exchange rate within the liquid phase and the interphase to the head space of the bioreactor is a critical process control parameter. Therefore, especially the air exchange between the sample liquid in the disposable bioreactor or the reagent container and the supernatant air should be improved.

DE 692 33 170 T2, DE 21 34 808 C3 and DE 1 140 755 A disclose reagent containers having vertical ribs or fins on their walls. The ribs are used to shake the solid phase reagent within the container. Shaking and the shake ribs are intended to preserve the homogeneity of the solid phase reagent, or to be more precise the ribs are intended to prevent or reduce the rotation or circulatory movement of the sample liquid and, when a stirrer is used, to improve the stirring through turbulence of the liquid.

The disadvantage with existing shake ribs is that, in relation to a cultivation of cells in a nutrient medium, such ribs can lead to an impairment of the cell-dividing process. The shearing forces generated lead to cell damage in the event of larger turbulences.

It is an object of the present invention to improve the disposable bioreactor or known reagent container such that, on the one hand, cell division is not impaired and, on the other, the gas exchange rate between the liquid and the supernatant air is improved such that a higher cell density is made possible.

We have found that this object is achieved in conjunction with a disposable bioreactor for cultivation of cells in a nutrient medium when the at least one chicane or baffle is configured as a web extending upwardly in the vertical direction.

The use of at least one chicane configured as a web ensures that, in the orbital shaking of the disposable bioreactor or of the reagent container, the surface of a contained liquid is broken up, making a higher rate of air exchange possible between the liquid and the supernatant air. And avoids shearing forces leading to cell damage. This leads to an increased input of oxygen into the liquid. When this liquid contains a nutrient medium with appropriate hybridoma cells, producing human cells or antibodies for example, a higher cell density is obtained, which results in higher product titers.

In a preferred embodiment of the present invention, the web has a cross section with a convex curvature directed away from the container's inner wall. The convex curvature not only avoids sharp edges, which can lead to an impairment of cell division and damage to the cells, but is also sufficient to obtain a higher gas exchange rate.

Preferably the web is configured in a helical shape.

In a further preferred embodiment of the present invention, the web is insertable into the reagent container as a separate part. This has the advantage that customary known reagent containers can be used, into which the webs are simple and inexpensive to insert. The web may have a round or oval cross section. It is also possible to use a kind of planeconvex cross section, in which case the plane side is adapted to the container wall, so that a slightly bioconvex cross section can also be used, depending on the pitch of the web and the internal diameter of the reagent container.

In a further preferred embodiment of the present invention, the web is molded onto the container's inner wall as a convex bulge. The web may have a cross section which is configured as an elliptical, parabolic or circular section.

In a further preferred embodiment of the present invention, the web is rounded off at the transition to the container's inner wall. This avoids sharp-cornered edges in the region of the web base as well.

In a further preferred embodiment of the present invention, the ratio of the web depth, which is radial to the container's inner wall, to the web width, which is transverse to the longitudinal axis of the web, is between 1:2 and 2:1. In a further preferred embodiment, the ratio of web depth to web width is about 1:1.

In a further preferred embodiment of the present invention, the web rises relative to a horizontal by a pitch angle between 30° and 60°, for example 45°. In principle, however, it is also possible to choose a pitch angle between 10° and 90°. A pitch of 90° is possible in particular when the ratio of web depth to web width is not greater than 2:1.

In a further preferred embodiment of the present invention, the lid of the reagent container is provided with at least one opening which is covered by a membrane making a sterile exchange of air possible.

Further details of the present invention will be apparent from the following extensive description and the accompanying drawings, in which preferred embodiments of the present invention are illustrated by way of example.

Figure 2:
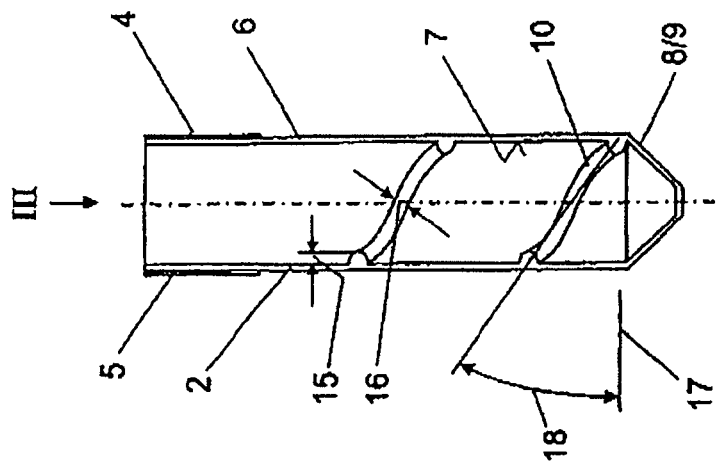
Figure 1:
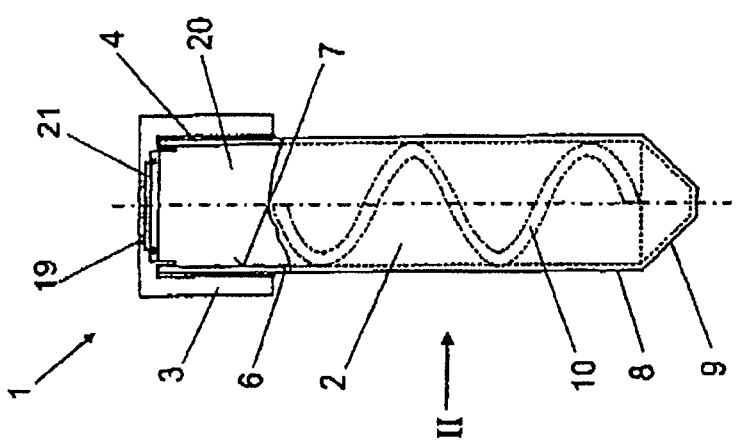

In the drawings:

FIG. 1 shows a side view of a disposable bioreactor with lid, partly in section, FIG. 2 shows a side view of the reagent container of FIG. 1 from direction II in section, FIG. 3 shows a plan view of the reagent container of FIG. 2 from direction III, FIG. 4 shows a side view of a further disposable bioreactor with lid and inserted separate web, FIG. 5 shows a side view of the web of FIG. 4, FIG. 6 shows a side view in section and detail in enlarged depiction of a web molded onto the container wall, FIG. 7 shows a side view in section and detail in enlarged depiction of a web molded onto an inner wall, FIG. 8 shows a side view in section and detail in enlarged depiction of a planeconvex separate web, and FIG. 9 shows a side view in section and detail in enlarged depiction of a separate web having a round cross section.

A disposable bioreactor 1 for cultivation of cells in a nutrient medium consists essentially of a reagent container 2 and a lid 3. The disposable bioreactor 1 is insertable with its reagent container 2 into a shaking apparatus (not depicted) and can be subjected to a shaking operation therein.

The reagent container 2 has at its upper end 4 a thread 5 for threaded union with the lid 3. The reagent container 2 further has a cylindrical container wall 6 having a container inner wall 7. The container wall 6 has a slightly conical configuration in the direction of its lower end 8, which is remote from its upper end 4. The lower end 8 is terminated by a conical tip 9.

In accordance with the embodiments corresponding to FIGS. 1 to 3, 6 and 7, a chicane or web 10 is molded onto the container inner wall 7. The web 10 (see FIG. 6) has a convex curvature 11 directed away from the container inner wall 7. According to FIG. 6, the cross section of the web 10 is configured as an elliptical section 12.

The cross section of a web 10' likewise has a convex curvature 11 which, after a short straight transition, transitions via a radius 13 into the container inner wall 7'. According to FIGS. 4 and 5, the web 14 is configured as a separate part. That is, the web 14 is insertable into the reagent container 2'' as a separate part.

In accordance with an embodiment according to FIG. 8, the separate web 14 which rests against the container inner wall 7'' is configured with a circular cross section.

According to FIG. 9, the cross section of the web 14' is configured planeconvex or as an elliptical section 12''.

The web 10 has a web depth 15 in the radial direction toward the container inner wall 7. Transversely to web depth 15, the web 10 has a web width 16.

The web 10 rises by a pitch angle 18 relative to a horizontal 17. In the example according to FIG. 2, the pitch angle 18 amounts to about 34°.

The lid 3 has five differently sized openings 19 which are covered by a membrane 21 in the direction of the container interior 20. The pore size of membrane 21 is 0.22 μm for example.

We claim:

1. A disposable bioreactor (1, 1') for cultivation of cells in a nutrient medium, comprising a reagent container (2, 2'') having an open upper end (4) that is sealable with a lid (3), the lid (3) being provided with at least one opening (19) that is covered by a membrane (21) for achieving a sterile exchange of air, the container (2, 2'') further having a lower end (8) and a container side wall (6) extending between the upper and lower ends (4, 8), a closed bottom wall (9) at the lower end (8) of the container side wall (6), the reagent container (2, 2'') being subjectable to a shaking operation in a shaking apparatus, the container side wall (6) having a substantially cylindrical inner surface extending from the open upper end (4) to the lower end (8), the cylindrical inner surface (7, 7', 7'') being interrupted only by a baffle (10, 10', 14, 14') consisting of as a single continuous uninterrupted web extending helically from a lower position in proximity to the lower end (8) to an upper position in proximity to the open upper end (4), the web (10, 14) having a cross-section with a convex curvature (11) directed away from the inner surface (7, 7', 7'') of the container wall (6) and configured as an elliptical, parabolic or circular section to avoid sharp edges that can impair cell division and damage cells.

2. The disposable bioreactor according to claim 1, wherein the substantially cylindrical inner surface of the container side wall (6) has a uniform inside diameter from the open upper end (4) of the container (2, 2'') substantially to the closed bottom wall (9), the web (14, 14') being formed separately from the container (2, 2'') and having an outer helical surface defining an outside diameter substantially equal to the inside diameter of the cylindrical inner surface of the container sidewall (6) so that the web (14, 14') is insertable into the open upper end (4) of the reagent container (2, 2') so that the outer helical surface of the web (14, 14') is positioned adjacent the substantially cylindrical inner surface substantially from the open upper end (4) to the lower end (8).

3. The disposable bioreactor according to claim 1, wherein the web (10, 10') is molded onto the inner surface (7, 7') of the container wall (6) as a convex bulge.

4. The disposable bioreactor according to claim 1, wherein the web (10', 14') is rounded off concavely at a transition to the inner surface (7') of the container wall (6).

5. The disposable bioreactor according to claim 1, wherein the ratio of the web depth (15), which is radial to the inner surface (7') of the container wall (6), to the web width (16), which is transverse to the longitudinal axis of the web, is between 1:2 and 2:1.

6. The disposable bioreactor according to claim 5, wherein the ratio of web depth (15) to web width (16) is 1:1.

7. The disposable bioreactor according to claim 1, wherein the web (10, 10', 14, 14') rises relative to a horizontal (17) by a pitch angle (18) between 10° and 90°.

8. The disposable bioreactor according to claim 7, wherein the pitch angle (18) is between 30° and 60°.

* * * * *